United States Patent
Jang et al.

(10) Patent No.: US 8,930,042 B2
(45) Date of Patent: Jan. 6, 2015

(54) MOBILIZED SENSOR NETWORK FOR STRUCTURAL HEALTH MONITORING

(75) Inventors: Jung Soon Jang, Bellevue, WA (US);
Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 152 days.

(21) Appl. No.: 13/183,580

(22) Filed: Jul. 15, 2011

(65) Prior Publication Data

US 2013/0018525 A1   Jan. 17, 2013

(51) Int. Cl.
*G06F 7/00* (2006.01)
*G06F 17/00* (2006.01)
*G06F 11/00* (2006.01)
*G01N 29/265* (2006.01)
*G01N 29/22* (2006.01)
*G01N 29/24* (2006.01)
*G01N 29/44* (2006.01)

(52) U.S. Cl.
CPC ............ *G01N 29/265* (2013.01); *G01N 29/225* (2013.01); *G01N 29/2475* (2013.01); *G01N 29/2481* (2013.01); *G01N 29/2493* (2013.01); *G01N 29/4427* (2013.01); *G01N 29/4472* (2013.01); *G01N 2291/0231* (2013.01); *G01N 2291/106* (2013.01); *G01N 2291/2694* (2013.01)
USPC ................. 701/2; 73/583; 73/865.8; 702/188

(58) Field of Classification Search
None
See application file for complete search history.

(56) References Cited

U.S. PATENT DOCUMENTS

| | | | |
|---|---|---|---|
| 5,504,345 A * | 4/1996 | Bartunek et al. ............ 250/559.4 |
| 6,060,853 A * | 5/2000 | Rongo et al. ............. 318/568.16 |
| 6,076,405 A | 6/2000 | Schoess |
| 6,378,387 B1 * | 4/2002 | Froom .......................... 73/865.8 |
| 6,637,266 B1 * | 10/2003 | Froom ............................ 73/583 |
| 2001/0032513 A1 * | 10/2001 | Havira et al. .................... 73/636 |
| 2005/0075846 A1 * | 4/2005 | Kim .................................. 703/1 |
| 2006/0069520 A1 * | 3/2006 | Gorinevsky et al. ............ 702/36 |
| 2006/0259217 A1 * | 11/2006 | Gorinevsky et al. ............ 701/29 |
| 2007/0006658 A1 * | 1/2007 | Kennedy et al. ................ 73/622 |
| 2007/0118335 A1 * | 5/2007 | Andarawis et al. ........... 702/188 |
| 2007/0261493 A1 * | 11/2007 | Kim ................................ 73/594 |
| 2007/0265790 A1 * | 11/2007 | Sealing et al. .................. 702/33 |
| 2007/0265806 A1 * | 11/2007 | Kim .............................. 702/187 |

(Continued)

FOREIGN PATENT DOCUMENTS

| | | |
|---|---|---|
| EP | 1744157A2 A2 | 1/2007 |
| WO | WO9219963 A1 | 11/1992 |
| WO | WO0150097 A2 | 7/2001 |
| WO | WO03005017 A2 | 1/2003 |

OTHER PUBLICATIONS

U.S. Appl. No. 12/897,158, filed Oct. 4, 2010, Jang.

(Continued)

*Primary Examiner* — Calvin Cheung
*Assistant Examiner* — Krishnan Ramesh
(74) *Attorney, Agent, or Firm* — Yee & Associates, P.C.

(57) ABSTRACT

A method and apparatus for inspecting an object is provided. Movement of inspection vehicles relative to a surface of the object is controlled using a controller. Generation of data about the object by sensor systems configured to generate the data when the sensor systems are in a configuration with respect to a location on the object for inspection and receiving power from the inspection vehicles is controlled using the controller. The data generated by the sensor systems is stored.

20 Claims, 10 Drawing Sheets

(56) References Cited

U.S. PATENT DOCUMENTS

| | | | |
|---|---|---|---|
| 2007/0266788 A1* | 11/2007 | Kim | 73/588 |
| 2009/0204344 A1* | 8/2009 | Daraio et al. | 702/39 |
| 2010/0162825 A1* | 7/2010 | Karp et al. | 73/799 |
| 2010/0217544 A1* | 8/2010 | Yan et al. | 702/56 |
| 2010/0235037 A1* | 9/2010 | Vian et al. | 701/29 |
| 2010/0312387 A1 | 12/2010 | Jang et al. | |
| 2010/0318243 A1* | 12/2010 | Lewis et al. | 701/3 |
| 2011/0018686 A1* | 1/2011 | Fahley et al. | 340/10.1 |
| 2011/0033254 A1* | 2/2011 | Abrams | 408/1 R |
| 2011/0154903 A1* | 6/2011 | Finkel et al. | 73/598 |
| 2012/0081540 A1 | 4/2012 | Jang | |
| 2013/0261876 A1* | 10/2013 | Froom et al. | 701/29.3 |

OTHER PUBLICATIONS

PCT search report dated Oct. 26, 2012 regarding application PCT/US2012/036360, filed May 3, 2012, applicant The Boeing Company, 18 pages.

Fujiwara et al., "An Articulated Multi-Vehicle Robot for Inspection and Testing of Pipeline Interiors," Proceedings of the 1993 IEEE/RSJ International Conference on Intelligent Robots and Systems, vol. 1, Jul. 1993, pp. 509-516.

* cited by examiner

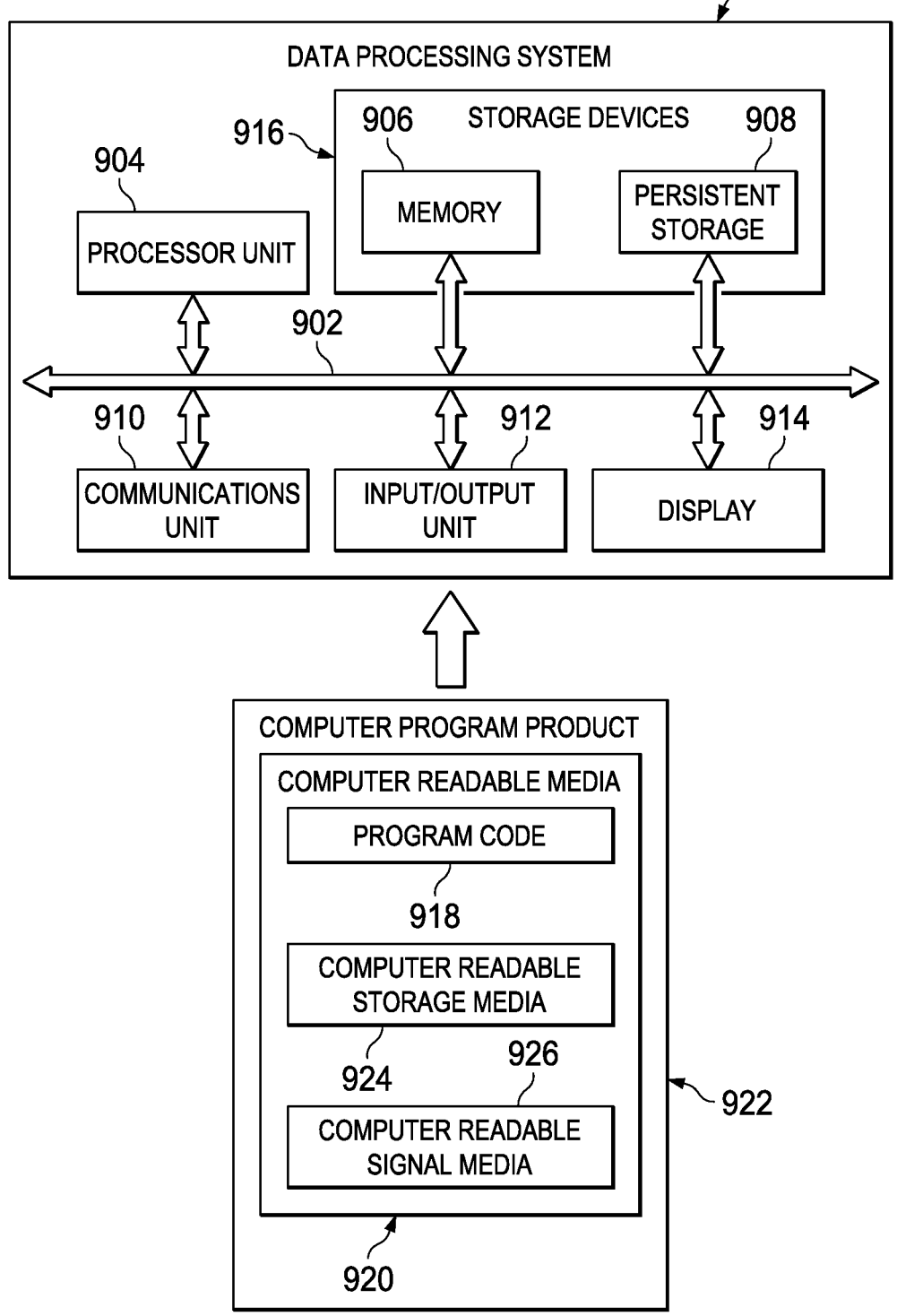

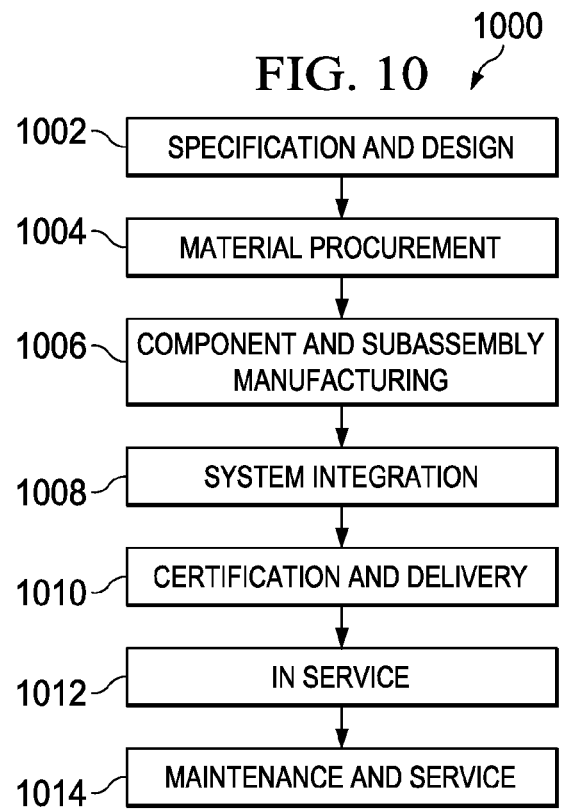
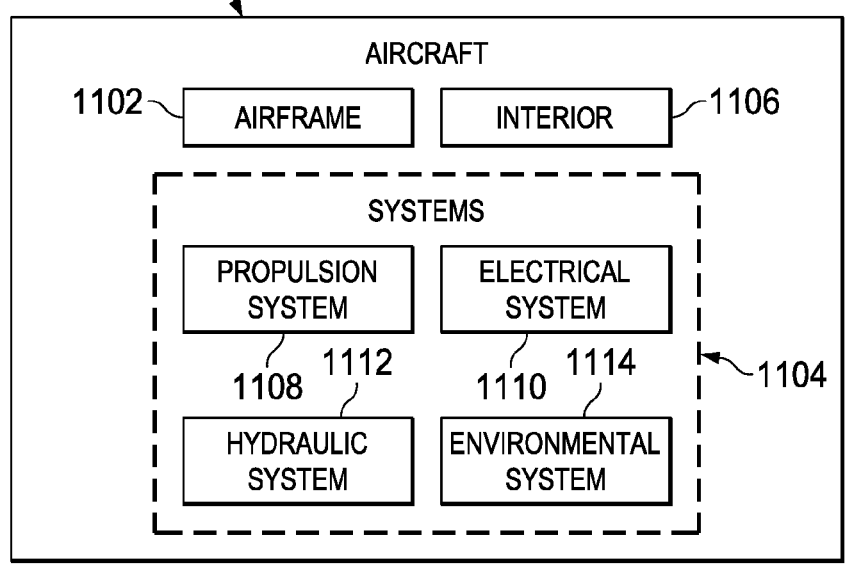

MOBILIZED SENSOR NETWORK FOR STRUCTURAL HEALTH MONITORING

BACKGROUND INFORMATION

1. Field

The present disclosure relates generally to inspecting objects and, in particular, to structural health monitoring of objects. Still more particularly, the present disclosure relates to a method and apparatus for a sensor system used to perform structural health monitoring of aircraft.

2. Background

Structural health monitoring involves detecting inconsistencies that may be present in an object. In particular, structural health monitoring may be performed to detect undesired inconsistencies that may be present in an object, such as an aircraft. Structural health monitoring involves the placement of sensors in different locations of an aircraft. Sensors may be attached to different locations on the aircraft or integrated as part of different structures in the aircraft.

With a structural health monitoring system, the different sensors at the different locations may provide data used to determine whether the different structures in the aircraft have a desired condition. In other words, this system may be used to identify undesired inconsistencies. When undesired inconsistencies are identified, rework and/or replacement of a structure may be performed.

In some cases, currently available monitoring systems may not provide as many features as desired for performing certain types of testing. For example, these systems may not provide as many features as desired for non-destructive evaluation (NDE) testing.

Therefore, it would be advantageous to have a method and apparatus that takes into account some of the issues discussed above, as well as other possible issues.

SUMMARY

In one advantageous embodiment, an apparatus comprises inspection vehicles, sensor systems, and a controller. The inspection vehicles are configured to move relative to a surface of an object and transmit data generated about the object. The sensor systems are configured to generate the data about the object when the sensor systems are in a configuration with respect to a location on the object for inspection and when receiving power from the inspection vehicles. The controller is configured to control movement of the inspection vehicles, control operation of the sensor systems to generate the data, and receive the data transmitted by the inspection vehicles.

In another advantageous embodiment, a health monitoring system comprises inspection vehicles, sensor systems, and a controller. The inspection vehicles are configured to move relative to a surface of an object and transmit data generated about the object. The sensor systems are associated with the inspection vehicles and configured to generate the data about the object. The controller is configured to control movement of the inspection vehicles into a configuration with respect to a location for inspection. The controller is configured to control operation of the sensor systems to generate the data about the object for the location. The controller is configured to receive the data transmitted by the inspection vehicles.

In yet another advantageous embodiment, a method for inspecting an object is provided. Movement of inspection vehicles relative to a surface of an object is controlled using a controller. Generation of data about the object by sensor systems configured to generate the data when the sensor systems are in a configuration with respect to a location on the object for inspection and receiving power from the inspection vehicles is controlled using the controller. The data generated by the sensor systems is stored.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

FIG. 9 is an illustration of a data processing system in accordance with an advantageous embodiment;

FIG. 10 is an illustration of an aircraft manufacturing and service method in accordance with an advantageous embodiment; and FIG. 11 is an illustration of an aircraft in which an advantageous embodiment may be implemented.

DETAILED DESCRIPTION

Figure 1:
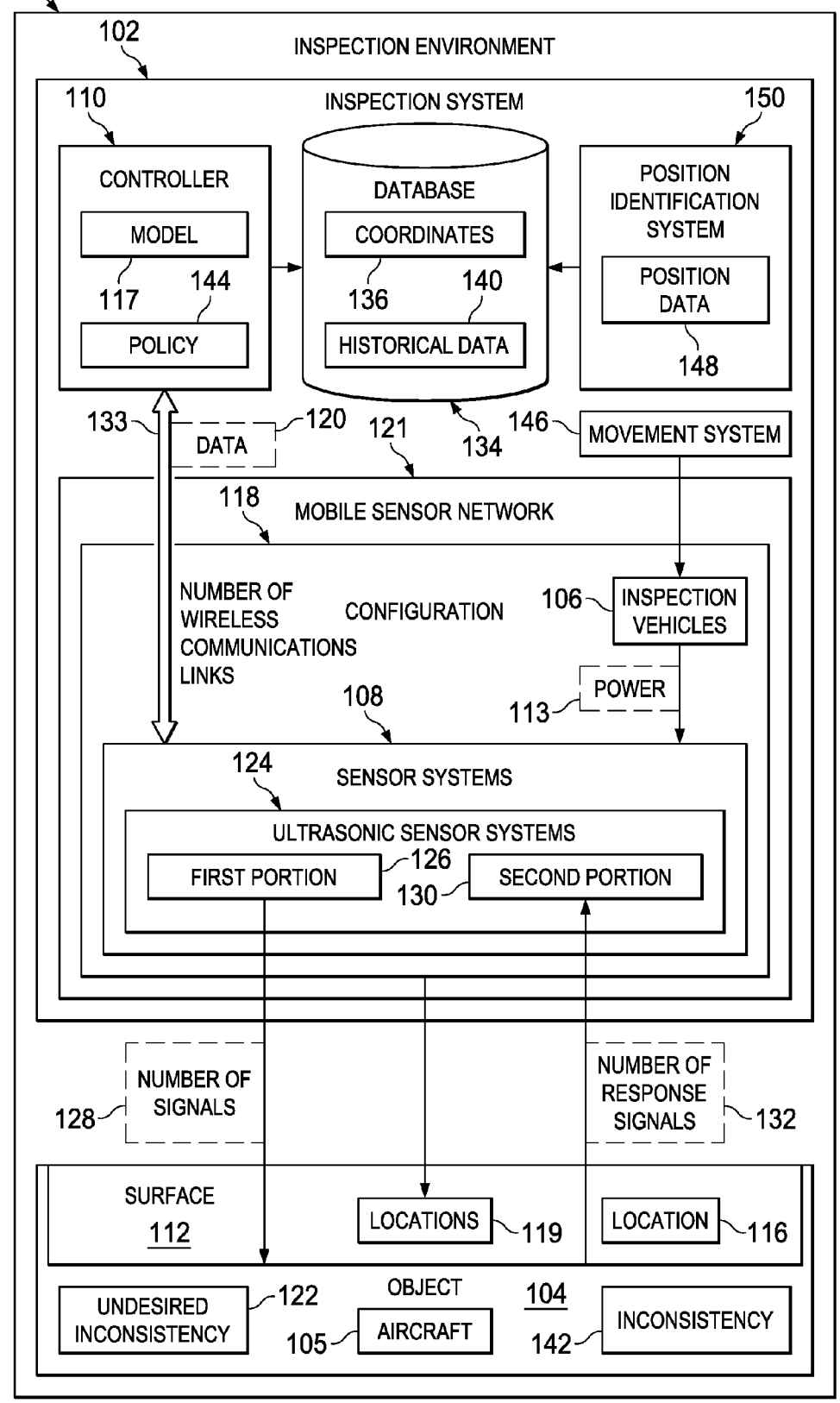
FIG. 1 is an illustration of an inspection environment in accordance with an advantageous embodiment.

The different advantageous embodiments recognize and take into account one or more different considerations. For example, the different advantageous embodiments recognize and take into account that an integrated structural health monitoring system may increase the weight and cost for each aircraft. With multiple aircraft, the structural health monitoring system may be integrated in each of those aircraft.

The different advantageous embodiments also recognize and take into account that with a structural health monitoring system that is integrated in an aircraft, other issues may occur in addition to weight and cost. For example, the different advantageous embodiments recognize and take into account that sensors may not operate as desired. The maintenance and/or replacement of sensors and other components may not be as easy as desired.

However, these types of structural health monitoring systems may be desirable for use in locations of an aircraft that may not be easily accessible for testing. For example, when testing the health of a structure inside a wing or a fuel system in an aircraft, a human operator or robotic vehicle may be unable to access the locations for testing as easily as desired. Additionally, a human operator or robotic vehicle may be unable to perform testing during flight of the aircraft. In these situations, an integrated structural health monitoring system may be desirable even though additional weight and/or cost may be added.

The different advantageous embodiments recognize and take into account that operators may use devices to inspect the aircraft that do not cause undesired inconsistencies on the surface of the aircraft or in the structures of the aircraft that may require rework or replacement of components. This type of inspection may be referred to as nondestructive inspection.

Using nondestructive inspection, issues, such as weight and cost, may be reduced, because the testing devices are not carried on the aircraft during flight. Further, the same devices may be used for multiple aircraft. As a result, the costs needed to inspect aircraft may be reduced through this type of testing.

The different advantageous embodiments also recognize and take into account, however, that nondestructive inspection is time and labor intensive. The different advantageous embodiments also recognize and take into account that this type of testing may be more difficult as a result of the design of the aircraft. The different advantageous embodiments recognize and take into account that testing may be need to be performed in areas that may be difficult for a human operator to reach. The assembly of a portion of the aircraft may be required in some cases to perform inspections.

The different advantageous embodiments also recognize and take into account that some of the types of testing performed by structural health monitoring systems may be more difficult or may not be performed using nondestructive inspection. For example, the different advantageous embodiments recognize and take into account that sensors in a structural health monitoring system may be configured to transmit signals and receive signals in the structure of the aircraft. The different advantageous embodiments recognize and take into account that placement and coordination of these types of sensors by human operators may be more difficult and may take more time than desired.

Further, repeatability of testing also may be more difficult. Positioning devices to perform nondestructive inspection often requires the operators to locate the same locations as a prior test. This type of repeatability may be more difficult with human operators placing the devices for nondestructive inspection.

The different advantageous embodiments recognize and take into account that quality of inspection depends on factors, such as human inference, precedence-based management processes, and experience. The different advantageous embodiments also recognize and take into account that nondestructive inspections, may not be designed to provide the information needed to support major inspection such as letter checks for aircraft.

Thus, the different advantageous embodiments provide a method and apparatus for inspecting an object. In particular, one or more of the advantageous embodiments may be used to perform inspection of an object, such as an aircraft.

In one advantageous embodiment, an apparatus comprises inspection vehicles, sensor systems, and a controller. The inspection vehicles are configured to move relative to a surface of an object and transmit data generated about the object. The sensor systems are configured to generate the data about the object when the sensor systems are in a configuration with respect to a location on the object for inspection and receiving power from the inspection vehicles. The controller is configured to control movement of the inspection vehicles, control operation of the sensor systems to generate the data, and receive the data transmitted by the inspection vehicles.

With reference now to the figures and, in particular, with reference to FIG. 1, an illustration of an inspection environment is depicted in accordance with an advantageous embodiment. In this illustrative example, inspection environment 100 includes inspection system 102. Inspection system 102 is used to perform inspection of object 104. In these illustrative examples, object 104 may take the form of aircraft 105.

As depicted, inspection system 102 comprises inspection vehicles 106, sensor systems 108, and controller 110. Inspection vehicles 106 are configured to move relative to surface 112 of object 104. This movement may be on surface 112, over surface 112, and/or under surface 112.

In these illustrative examples, controller 110 is configured to control movement of inspection vehicles 106 relative to surface 112 of object 104. In particular, controller 110 is configured to control movement of inspection vehicles 106 relative to each other on surface 112 of object 104. Controller 110 is configured to control movement of inspection vehicles 106 in a coordinated fashion. Controller 110 may be implemented using a computer system, a processor, an application specific integration circuit, or some other type of circuit system.

In these illustrative examples, inspection vehicles 106 are configured to send power 113 to sensor systems 108 to operate sensor systems 108. For example, each inspection vehicle in inspection vehicles 106 sends power to a corresponding sensor system in sensor systems 108. Power 113 may be sent to sensor systems 108 using conductive power transfer, inductive power transfer, and/or some other suitable type of power transfer.

Sensor systems 108 may be associated with inspection vehicles 106 and/or object 104 in these examples. As one illustrative example, an inspection vehicle in inspection vehicles 106 may be associated with a sensor system in sensor systems 108.

This association, in these illustrative examples, is a physical association. A first component, such as a sensor system, may be considered to be associated with a second component, such as an inspection vehicle, by being secured to the second component, bonded to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

As another illustrative example, a sensor system in sensor systems 108 may be associated with object 104. For example, sensor systems 108 may be attached to surface 112 of object 104, embedded within object 104, and/or associated with object 104 in some other suitable manner. Thus, all of sensor systems 108 may be associated with inspection vehicles 106, all of sensor systems 108 may be associated with object 104, or a first portion of sensor systems 108 may be associated with some inspection vehicles 106, while a second portion of sensor systems 108 may be associated with object 104.

Controller 110 is configured to identify location 116 on object 104 for inspection. Inspection of object 104 may be performed for surface 112 at location 116 and/or one or more structures of object 104 under surface 112 at location 116. Location 116 may be identified using model 117 of object 104. Model 117 may be a design of object 104, such as, for example, without limitation, a three-dimensional computer-aided design model.

The inspection of object 104 at location 116 is performed using inspection vehicles 106 and sensor systems 108. When sensor systems 108 are associated with inspection vehicles 106, movement of inspection vehicles 106 moves sensor systems 108. As a result, controller 110 may control inspection vehicles 106 to move sensor systems 108 into configuration 118 with respect to location 116.

In particular, sensor systems 108 may be moved to locations 119 on object 104 relative to location 116. Locations 119 for sensor systems 108 on object 104 form configuration 118. Locations 119 may include at least one of a location around location 116, a location within a selected distance from location 116, a location over location 116, location 116, and a location relative to location 116 in some other suitable manner.

As used herein, the phrase "at least one of", when used with a list of items, means different combinations of one or more of the listed items may be used, and only one of each item in the list may be needed. For example, "at least one of item A, item B, and item C" may include, for example, without limitation, item A, or item A and item B. This example also may include item A, item B, and item C, or item B and item C. In other examples, "at least one of" may be, for example, without limitation, two of item A, one of item B, and 10 of item C; four of item B and seven of item C; and other suitable combinations.

In some illustrative examples, sensor systems 108 may be associated with object 104 at locations 119. In this manner, sensor systems 108 may be in configuration 118 with respect to location 116 for inspection without requiring inspection vehicles 106 to move sensor systems 108 into configuration 118.

When sensor systems 108 are associated with object 104 at locations 119, controller 110 may control inspection vehicles 106 to move to locations 119. When inspection vehicles 106 are at locations 119, inspection vehicles 106 may send power 113 to sensor systems 108 to operate sensor systems 108.

In these depicted examples, sensor systems 108 and inspection vehicles 106 form mobile sensor network 121 when sensor systems 108 and inspection vehicles 106 are at locations 119 for configuration 118. Sensor systems 108 and/or inspection vehicles 106 may be moved relative to object 104 to reconfigure mobile sensor network 121 to have different configurations for testing different locations on object 104.

When sensor systems 108 and inspection vehicles 106 are in configuration 118 with respect to location 116 for inspection, and when sensor systems 108 receive power 113 from inspection vehicles 106, sensor systems 108 generate data 120 about object 104 for location 116. This generation of data 120 is part of the inspection of object 104 to determine whether undesired inconsistency 122 is present at location 116 on object 104.

In these illustrative examples, sensor systems 108 may take the form of ultrasonic sensor systems 124. Controller 110 may configure first portion 126 of ultrasonic sensor systems 124 to transmit number of signals 128 into object 104. Further, controller 110 may configure second portion 130 of ultrasonic sensor systems 124 to receive number of response signals 132. With this configuration of ultrasonic sensor systems, first portion 126 of ultrasonic sensor systems 124 transmits number of signals 128 into object 104. Number of response signals 132 is generated in response to number of signals 128 transmitted into object 104. Number of response signals 132 is received by second portion 130 of ultrasonic sensor systems 124. Number of response signals 132 forms data 120.

Sensor systems 108 are configured to transmit data 120 to inspection vehicles 106. When sensor systems 108 are associated with object 104 instead of inspection vehicles 106, this transmission may occur using a number of wireless communications links. When sensor systems 108 are associated with inspection vehicles 106, this transmission may occur using a number of wired, optical, wireless, and/or some other suitable type of communications link.

Inspection vehicles 106 transmit data 120 to controller 110. In particular, inspection vehicles 106 transmit data 120 to controller 110 over number of wireless communications links 133.

In response to receiving data 120 generated by sensor systems 108 for location 116, controller 110 stores data 120 in database 134. In particular, controller 110 stores data 120 in database 134 in association with coordinates 136 identifying location 116 for which data 120 was generated. This association between data 120 and coordinates 136 is a logical association. Coordinates 136 may be defined using, for example, a Cartesian coordinate system, a polar coordinate system, a three-dimensional coordinate system, and/or some other suitable coordinate system relative to object 104.

In these illustrative examples, database 134 includes historical data 140. Historical data 140 is for a number of inspections of object 104 at location 116 performed a number of times prior to the generation of data 120.

Data 120 and/or historical data 140 may be used to determine whether undesired inconsistency 122 is present in object 104. For example, data 120 generated by sensor systems 108 may indicate a presence of inconsistency 142. As one illustrative example, a difference between data 120 generated for location 116 and historical data 140 generated for location 116 may indicate inconsistency 142.

In these illustrative examples, inconsistency 142 may or may not be undesired inconsistency 122. Policy 144 may be applied to data 120 to determine whether inconsistency 142 is undesired inconsistency 122. Policy 144 may include a number of rules, criteria, and/or other suitable information that may be used in identifying undesired inconsistency 122.

As depicted, movement system 146 may be present in inspection environment 100 in some illustrative examples. In one illustrative example, movement system 146 may be part of inspection system 102. Movement system 146 may be configured to move inspection vehicles 106 relative to object 104.

In these illustrative examples, movement system 146 may be configured to place inspection vehicles 106 on object 104 such that inspection vehicles 106 may move relative to surface 112 of object 104. For example, movement system 146 may include at least one of a robotic arm system, a track system, a crane, a hoist, a number of platforms, and other suitable types of movement devices configured to move inspection vehicles 106.

Additionally, in some illustrative examples, controller 110 may use position data 148 received from position identification system 150 to control the movement of inspection vehicles 106. For example, position identification system 150 may include at least one of a number of camera systems, a number of position sensors, a range finder, and other suitable devices for identifying position data 148 for inspection vehicles 106. Position data 148 identifies the positions of inspection vehicles 106 relative to object 104.

The illustration of inspection environment 100 in FIG. 1 is not meant to imply physical or architectural limitations to the manner in which an advantageous embodiment may be implemented. Other components in addition to and/or in place of the ones illustrated may be used. Some components may be unnecessary. Also, the blocks are presented to illustrate some functional components. One or more of these blocks may be combined and/or divided into different blocks when implemented in an advantageous embodiment.

For example, in some illustrative examples, inspection system 102 may be used to test a number of other locations relative to object 104 in addition to and/or in place of location 116. For example, a first portion of inspection vehicles 106 may be used to test a wing of aircraft 105, while another portion of inspection vehicles 106 may be used to test a fuselage of aircraft 105.

In other illustrative examples, object 104 may be an object other than aircraft 105. Object 104 may be selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a manufacturing facility, a building, a wing, a fuselage, an engine housing, a skin panel, a structure, and/or some other suitable type of platform.

Figure 2:
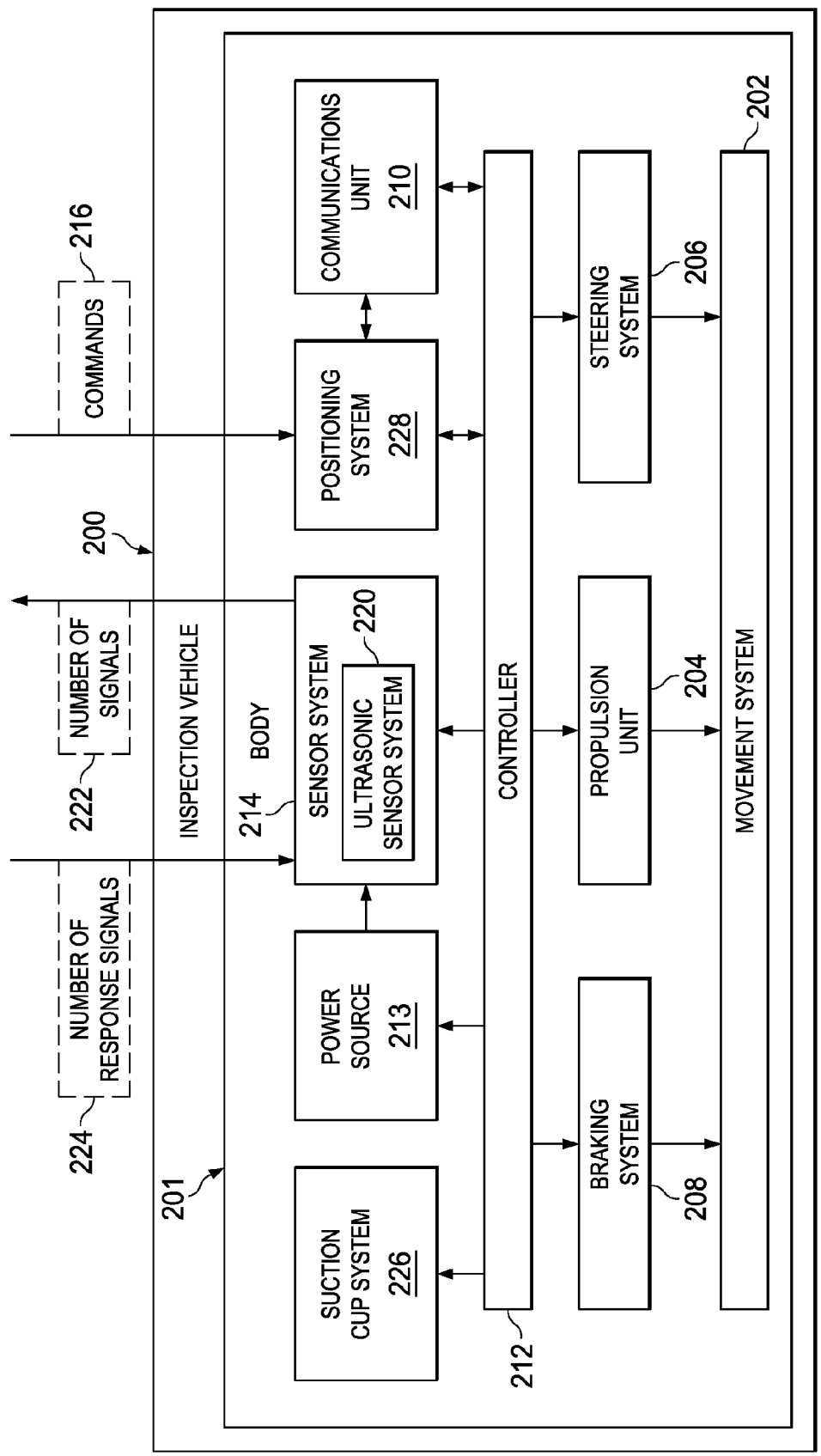
FIG. 2 is an illustration of components for an inspection vehicle in accordance with an advantageous embodiment.

With reference now to FIG. 2, an illustration of components for an inspection vehicle is depicted in accordance with an advantageous embodiment. In this illustrative example, inspection vehicle 200 is an example of one implementation for one of inspection vehicles 106 in FIG. 1. The different components illustrated in FIG. 2 for inspection vehicle 200 may be implemented using various components that are currently available for use in vehicles.

As illustrated, inspection vehicle 200 includes body 201, movement system 202, propulsion unit 204, steering system 206, braking system 208, communications unit 210, controller 212, power source 213, and sensor system 214. Body 201 provides a structure that other components in inspection vehicle 200 may be connected to in these examples. Body 201 may be, for example, without limitation, a frame, a uni-body, or some other suitable type of body.

Movement system 202 comprises components configured to provide movement of inspection vehicle 200. For example, movement system 202 may comprise at least one of wheels, continuous tracks, legs, rollers, sliders, propellers, fan blades, wings, and other suitable types of movement mechanisms.

Additionally, propulsion unit 204 is configured to cause movement by movement system 202. In other words, propulsion unit 204 generates mechanical energy for movement system 202. Propulsion unit 204 may be, for example, an electrical motor.

Steering system 206 is configured to control movement system 202 in different directions. Braking system 208 is used to slow and/or halt movement of movement system 202. Steering system 206 may change the direction in which movement system 202 moves inspection vehicle 200.

Communications unit 210 is configured to allow for the exchange of information. In particular, communications unit 210 allows the reception and transmission of information. For example, communications unit 210 allows commands to be received and data to be transmitted.

In these illustrative examples, communications unit 210 may be a wireless communications unit. In other illustrative examples, communications may be provided through a physical connection. With a physical connection, communications unit 210 may be, for example, a network interface card, a modem, or some other suitable type of communications unit.

In these illustrative examples, communications unit 210 allows for the exchange of information between controller 212 and controller 110 from FIG. 1. In these illustrative examples, controller 212 may be implemented using a processor, an application specific integration circuit, or some other type of circuit system.

As depicted, controller 212 is configured to receive commands 216 using communications unit 210. Commands 216 may be received from controller 110 in FIG. 1. In response to commands 216, controller 212 controls the operations of movement system 202, propulsion unit 204, steering system 206, braking system 208, and power source 213.

Power source 213 is configured to provide power to the various components in inspection vehicle 200. In these illustrative examples, power source 213 may send power to sensor system 214 based on commands 216 received from controller 212. Sensor system 214 is configured to operate when power is received from power source 213. Power may be sent to sensor system 214 using conductive power transfer, inductive power transfer, and/or some other suitable source of power transfer.

In these illustrative examples, sensor system 214 is associated with inspection vehicle 200. Sensor system 214 may be integrated as part of inspection vehicle 200, connected to inspection vehicle 200, and/or removably connected to inspection vehicle 200, depending on the particular implementation. In some cases, when sensor system 214 is removably connected to body 201 of inspection vehicle 200, this system may be considered to be a separate component from inspection vehicle 200.

As illustrated, sensor system 214 takes the form of ultrasonic sensor system 220. Ultrasonic sensor system 220 is a non-destructive inspection system in this depicted example. Ultrasonic sensor system 220 may be configured to transmit number of signals 222 into an object, such as object 104 in FIG. 1, and/or receive number of response signals 224. Number of response signals 224 is generated in the object in response to number of signals 222. These signals are ultrasonic signals in these illustrative examples.

In addition to these components, suction cup system 226 may be present in inspection vehicle 200 in some illustrative examples. Suction cup system 226 may aid in attaching inspection vehicle 200 to a surface of an object, such as surface 112 of object 104 in FIG. 1. Suction cup system 226 may be used in combination with or may be part of movement system 202 and may be controlled by controller 212.

Further, suction cup system 226 may be used to turn inspection vehicle 200. In this manner, inspection vehicle 200 may turn in different directions without moving forward or backward. As a result, sharper turns may be made using suction cup system 226 as compared to those made using movement system 202 and steering system 206.

Additionally, positioning system 228 also may be located in inspection vehicle 200 in some illustrative examples. Positioning system 228 may be configured to identify a position of inspection vehicle 200 with respect to the object. Positioning system 228 may include, for example, a global positioning system unit, an inertial measurement unit, a number of position sensors, and/or other suitable types of devices for identifying the position of inspection vehicle 200. Positioning system 228 may be configured to generate position data for inspection vehicle 200 that is sent to controller 110 in FIG. 1.

The illustration of inspection vehicle 200 in FIG. 2 is not meant to imply physical or architectural limitations to the manner in which an advantageous embodiment may be implemented. Other components in addition to and/or in place of the ones illustrated may be used. Some components may be unnecessary. Also, the blocks are presented to illustrate some functional components. One or more of these blocks may be combined and/or divided into different blocks when implemented in an advantageous embodiment.

For example, in some illustrative examples, inspection vehicle 200 may not include suction cup system 226 and/or positioning system 228. In other illustrative examples, inspection vehicle 200 may include components in addition to the components illustrated in FIG. 2. For example, inspection vehicle 200 may include a camera system configured to generate images of the surface of the object during testing. As another illustrative example, inspection vehicle 200 may include sensor systems in addition to sensor system 214.

In still other illustrative examples, sensor system 214 may not be associated with inspection vehicle 200. For example, inspection vehicle 200 may be configured to move to a location on an object at which a sensor system is attached to the surface of the object and/or embedded with the object.

Figure 3:
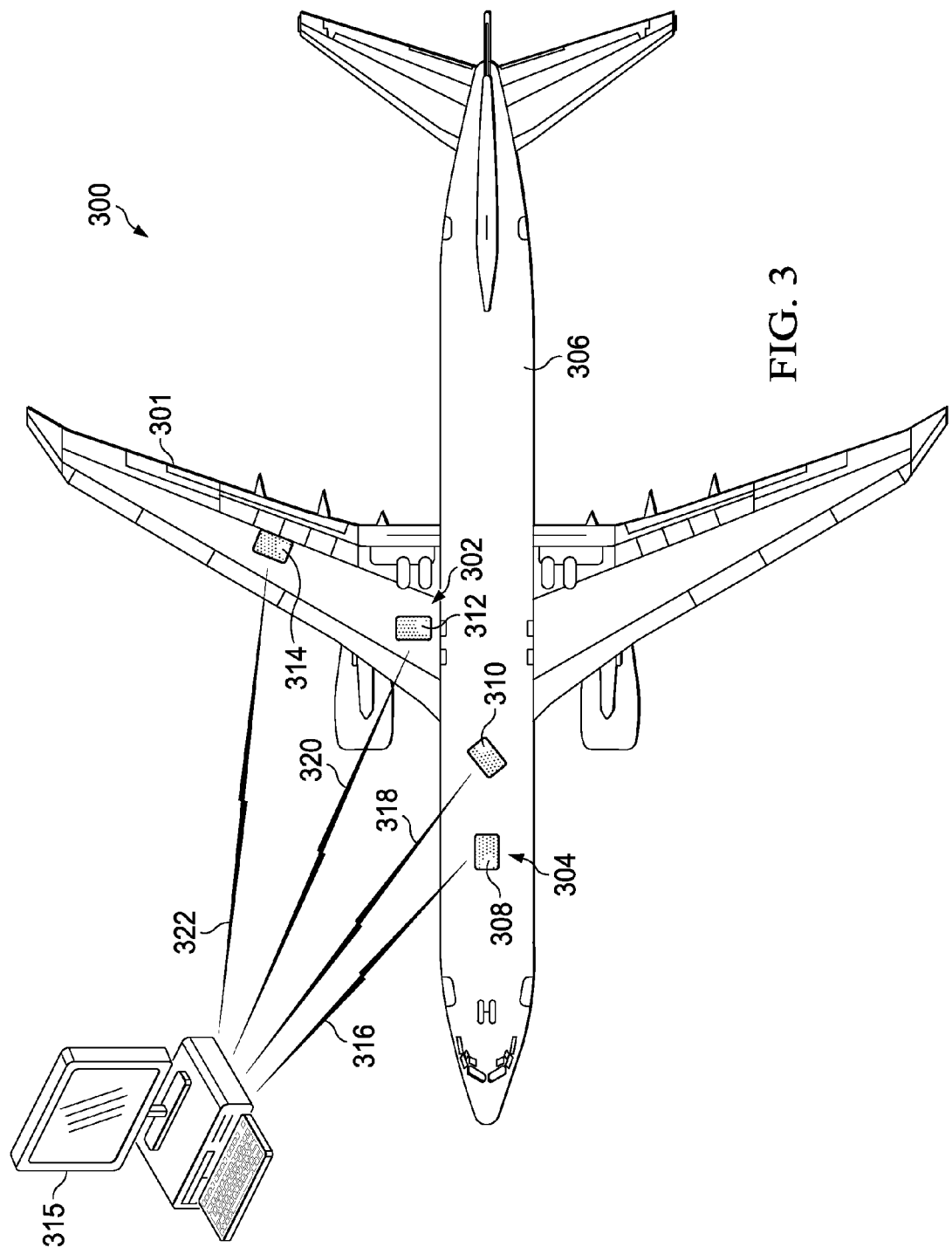
FIG. 3 is an illustration of an inspection environment in accordance with an advantageous embodiment.

With reference now to FIG. 3, an illustration of an inspection environment is depicted in accordance with an advantageous embodiment. In this illustrative example, inspection environment 300 is an example of a physical implementation for inspection environment 100 in FIG. 1.

Inspection environment 300 includes aircraft 301 and inspection system 302. Aircraft 301 is an example of one implementation for aircraft 105 in FIG. 1. As depicted, inspection system 302 is configured to perform an inspection of aircraft 301. Inspection system 302 is an example of one implementation for inspection system 102 in FIG. 1.

Inspection system 302 includes inspection vehicles 304. These inspection vehicles also may be referred to as robots or robotic vehicles. Inspection vehicles 304 are configured to move relative to surface 306 of aircraft 301. In particular, inspection vehicles 304 move on surface 306 of aircraft 301. Inspection vehicles 304 include inspection vehicle 308, inspection vehicle 310, inspection vehicle 312, and inspection vehicle 314. One or more of these inspection vehicles may be implemented using inspection vehicle 200 in FIG. 2.

Inspection vehicles 304 are configured to exchange information with controller 315. In particular, inspection vehicle 308, inspection vehicle 310, inspection vehicle 312, and inspection vehicle 314 are configured to exchange information with controller 315 using wireless communications link 316, wireless communications link 318, wireless communications link 320, and wireless communications link 322, respectively.

As one illustrative example, inspection vehicles 304 are configured to receive commands from controller 315 that control movement of inspection vehicles 304 on surface 306 of aircraft 301. Inspection vehicles 304 may be moved to various locations on aircraft 301 to perform inspection of aircraft 301. This inspection may be non-destructive inspection. In this illustrative example, inspection vehicles 304 are associated with sensor systems (not shown) configured to perform non-destructive inspection of aircraft 301.

Figure 4:
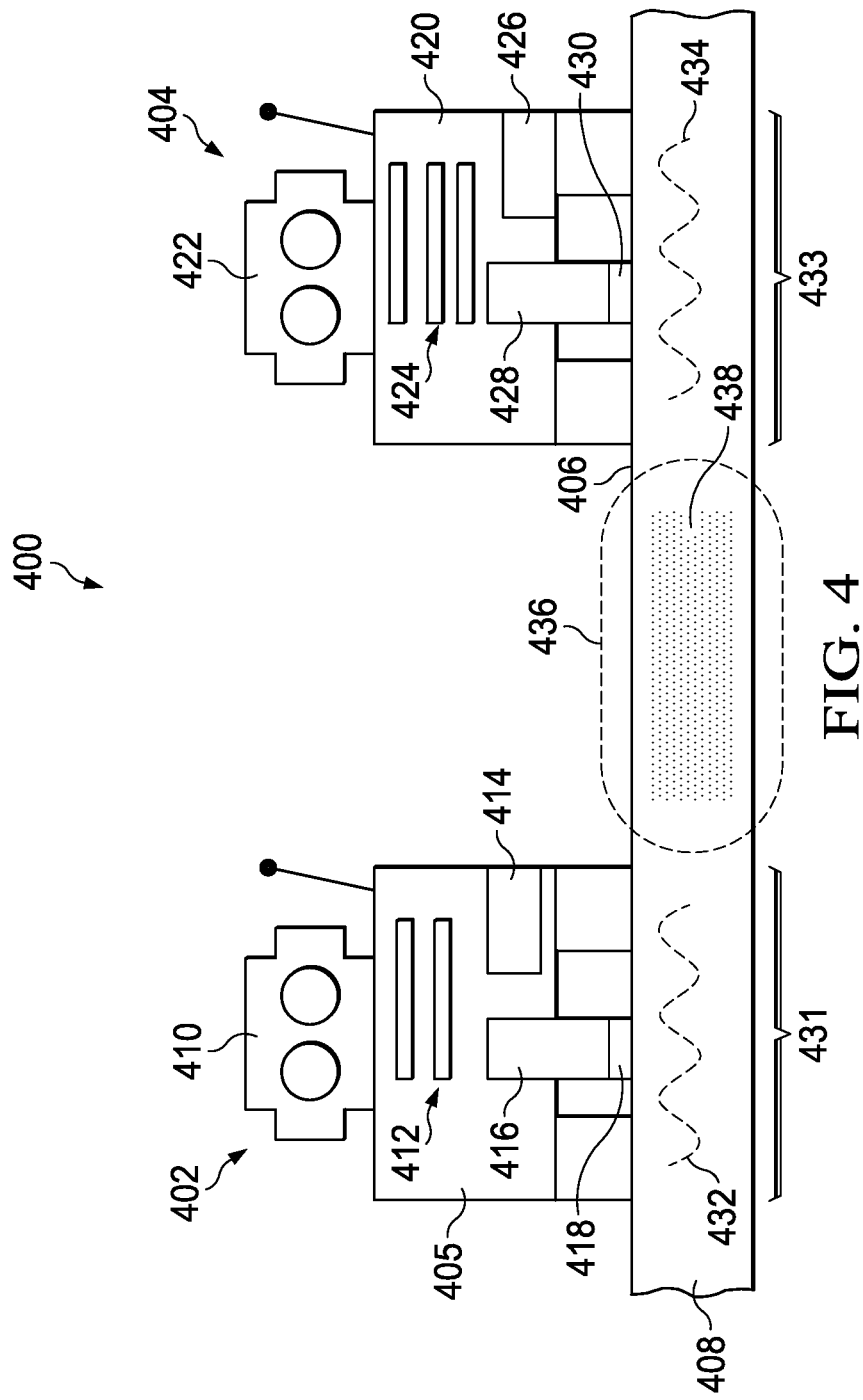
FIG. 4 is an illustration of another inspection environment in accordance with an advantageous embodiment.

With reference now to FIG. 4, an illustration of another inspection environment is depicted in accordance with an advantageous embodiment. In this illustrative example, inspection environment 400 is an example of a physical implementation for inspection environment 100 in FIG. 1. As depicted, inspection vehicle 402 and inspection vehicle 404 are present in inspection environment 400. Inspection vehicle 402 and inspection vehicle 404 are examples of a physical implementation for inspection vehicle 200 in FIG. 2.

Inspection vehicle 402 and inspection vehicle 404 are configured to move on surface 406 of object 408 in this illustrative example. Object 408 may be a structure for an aircraft, such as aircraft 105 in FIG. 1 and/or aircraft 301 in FIG. 3.

Inspection vehicle 402 comprises body 405, positioning system 410, communications unit 412, controller 414, and power source 416. Positioning system 410, communications unit 412, controller 414, and power source 416 are associated with body 405. In particular, positioning system 410, communications unit 412, controller 414, and power source 416 are located within body 405 of inspection vehicle 402.

Positioning system 410 is configured to identify a location of inspection vehicle 402 relative to object 408. Communications unit 412 is configured to allow information to be exchanged between controller 414 inside inspection vehicle 402 and another controller, such as controller 110 in FIG. 1 and/or controller 315 in FIG. 3. Controller 414 is configured to receive information, such as commands that control movement of inspection vehicle 402. Further, controller 414 is configured to transmit information in the form of data.

Power source 416 is configured to provide power to the various components of inspection vehicle 402. Further, power source 416 is configured to provide power to sensor system 418.

Sensor system 418 is associated with inspection vehicle 402 in this illustrative example. Inspection vehicle 402 with sensor system 418 is at location 431 on object 408. In particular, sensor system 418 is connected to power source 416.

Power source 416 may be connected to sensor system 418 and then later disconnected when power is not needed from power source 416. Power source 416 also may provide power to sensor system 418 through wireless transfer of power. For example, without limitation, electromagnetic induction, electromagnetic radiation, and/or on other suitable wireless power transfer mechanism may be used.

In a similar manner, inspection vehicle 404 comprises body 420, positioning system 422, communications unit 424, controller 426, and power source 428. Further, sensor system 430 is connected to power source 428. Inspection vehicle 404 with sensor system 430 is at location 433 on object 408.

As depicted, sensor system 418 is configured to transmit signal 432 into object 408. Sensor system 430 is configured to detect response signal 434 generated in response to signal 432 being transmitted in object 408. Response signal 434 is generated in response to signal 432 passing through portion 436 of object 408.

In this illustrative example, response signal 434 detected by sensor system 430 may be transmitted as data by inspection vehicle 404 to a controller, such as controller 110 in FIG. 1 and/or controller 315 in FIG. 3. This data may be used to determine whether inconsistency 438 in portion 436 of object 408 is an undesired inconsistency.

Figure 5:
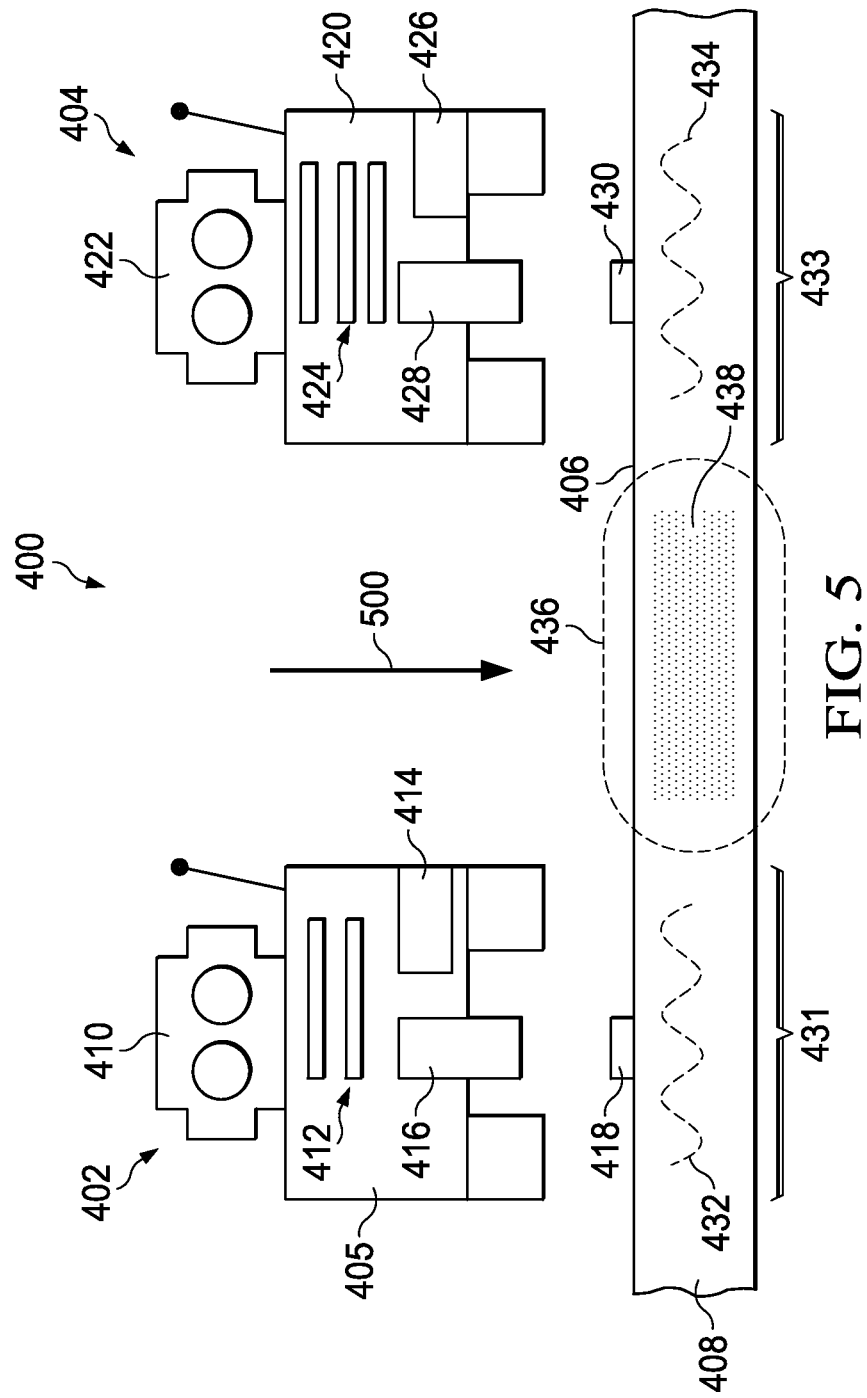
FIG. 5 is an illustration of an inspection environment in which sensor systems are associated with an object instead of inspection vehicles in accordance with an advantageous embodiment.

With reference now to FIG. 5, an illustration of an inspection environment in which sensor systems are associated with an object instead of inspection vehicles is depicted in accordance with an advantageous embodiment. In this illustrative example, sensor system 418 and sensor system 430 in inspection environment 400 from FIG. 4 are associated with object 408 instead of inspection vehicle 402 and inspection vehicle 404, respectively.

As depicted, sensor system 418 and sensor system 430 are attached to surface 406 of object 408 at location 431 and location 433, respectively, on object 408. Inspection vehicle 402 and inspection vehicle 404 may be moved over location 431 and location 433, respectively. Further, inspection vehicle 402 and inspection vehicle 404 may be moved in the direction of arrow 500 such that power source 416 and power source 428 come into contact with sensor system 418 and sensor system 430, respectively.

When power source 416 and power source 428 come into contact with sensor system 418 and sensor system 430, respectively, power is sent to these sensor systems. When receiving power, sensor system 418 is configured to send signal 432, and sensor system 430 is configured to detect response signal 434.

Figure 6:
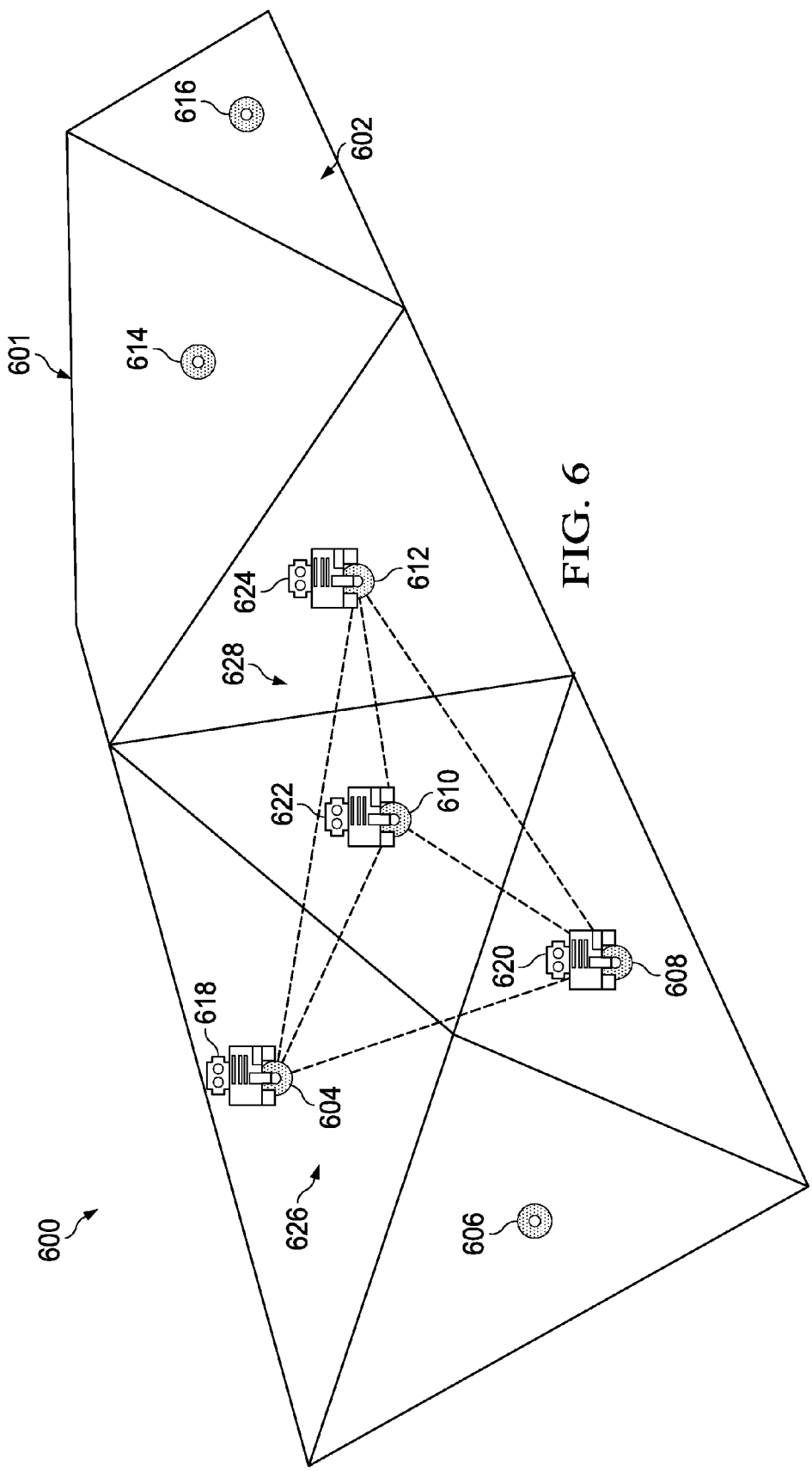
FIG. 6 is an illustration of yet another inspection environment in accordance with an advantageous embodiment.

With reference now to FIG. 6, an illustration of yet another inspection environment is depicted in accordance with an advantageous embodiment. In this illustrative example, inspection environment 600 is an example of one implementation for inspection environment 100 in FIG. 1. Wing section 601 is present in inspection environment 600. Wing section 601 is an example of one implementation for object 104 in FIG. 1.

Plurality of locations 602 on wing section 601 include locations identified as locations requiring inspection. Plurality of locations 602 includes locations 604, 606, 608, 610, 612, 614, and 616.

As depicted, inspection vehicles 618, 620, 622, and 624 have been moved to locations 604, 608, 610, and 612, respectively. Sensor systems (not shown) are associated with these inspection vehicles and are configured to perform non-destructive inspection of wing section 601. Inspection vehicles 618, 620, 622, and 624 at locations 604, 608, 610, and 612, respectively, form configuration 626 for mobile sensor network 628. Inspection vehicles 618, 620, 622, and 624 may be moved to other locations of plurality of locations 602 to form other configurations for mobile sensor network 628.

Figure 7:
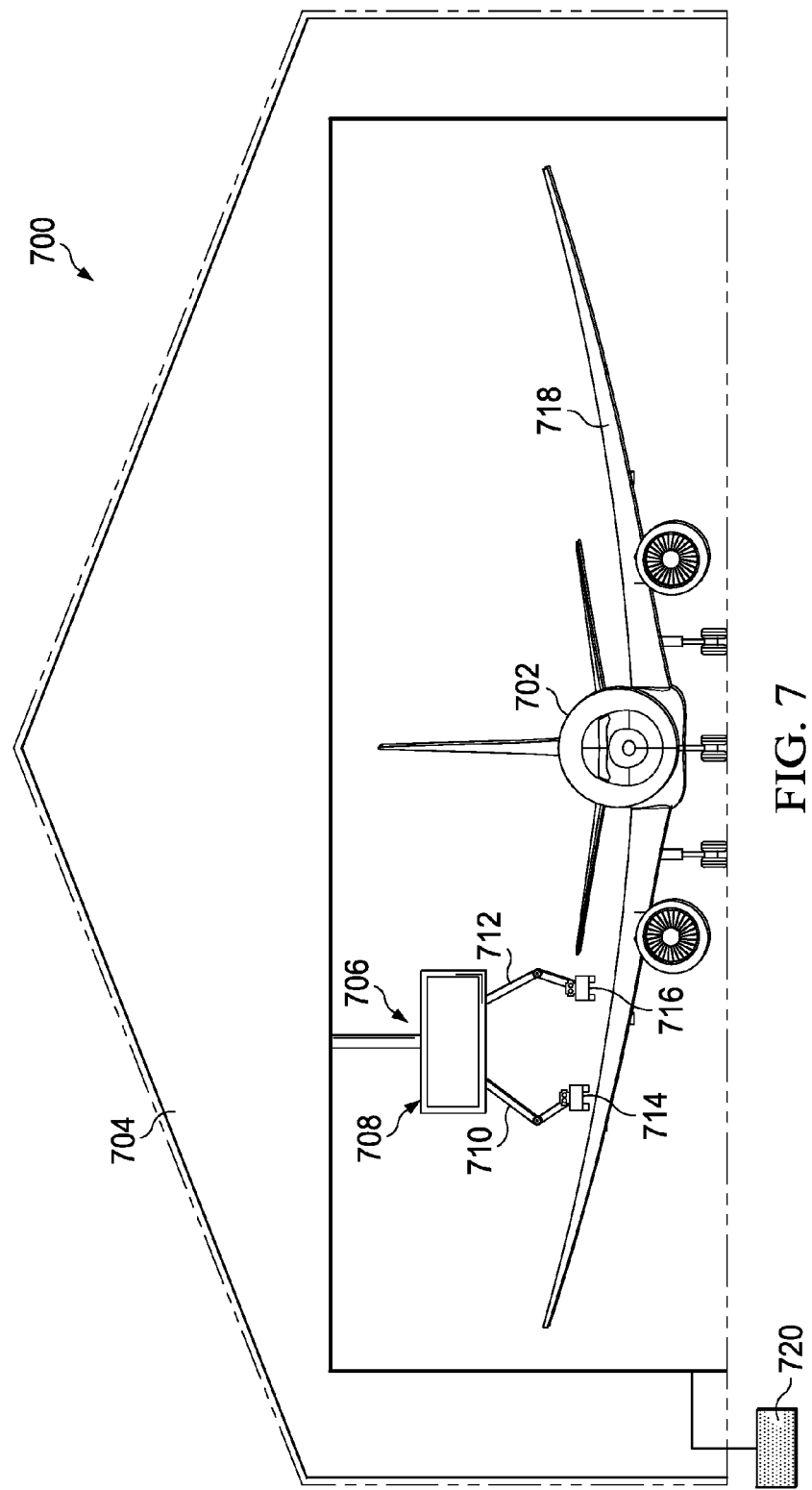
FIG. 7 is an illustration of an inspection environment in accordance with an advantageous embodiment.

With reference now to FIG. 7, an illustration of an inspection environment is depicted in accordance with an advantageous embodiment. In this illustrative example, inspection environment 700 is an example of one implementation for inspection environment 100 in FIG. 1.

As depicted, aircraft 702 is being inspected within hangar 704 in inspection environment 700. Movement system 706 is associated with hangar 704. Movement system 706 comprises robotic system 708. Robotic system 708 is configured to pick up, hold, and release inspection vehicles.

For example, robotic system 708 has robotic arm 710 and robotic arm 712. Robotic arm 710 and robotic arm 712 may be used to pick up and hold inspection vehicle 714 and inspection vehicle 716, respectively. Further, robotic arm 710 and robotic arm 712 may place inspection vehicle 714 and inspection vehicle 716 onto surface 718 of aircraft 702. Inspection vehicle 714 and inspection vehicle 716 may be implemented using inspection vehicle 200 in FIG. 2.

Once inspection vehicle 714 and inspection vehicle 716 are placed onto aircraft 702, these inspection vehicles may move on surface 718 to different locations on aircraft 702 to perform non-destructive inspection. Data generated during this non-destructive inspection may be sent to controller 720 using wireless communications.

As yet another illustrative example, robotic arm 710 and robotic arm 712 in robotic system 708 may be used without inspection vehicle 714 and inspection vehicle 716. For example, robotic arm 710 and robotic arm 712 may be associated with sensor systems 108 in FIG. 1.

In this depicted example, controller 720 sends locations for the inspection to robotic system 708. Robotic system 708 moves robotic arm 710 and robotic arm 712 with respect to surface 718 to different locations on aircraft 702 to perform non-destructive inspection. Robotic system 708, for example, can be moved by different mechanisms that may be included in movement system 706 with robotic arm 712. These mechanisms may include, for example, a track and crane system, as well as other appropriate systems. A crane may hold robotic system 708 and may move along a track with respect to aircraft 702.

Figure 8:
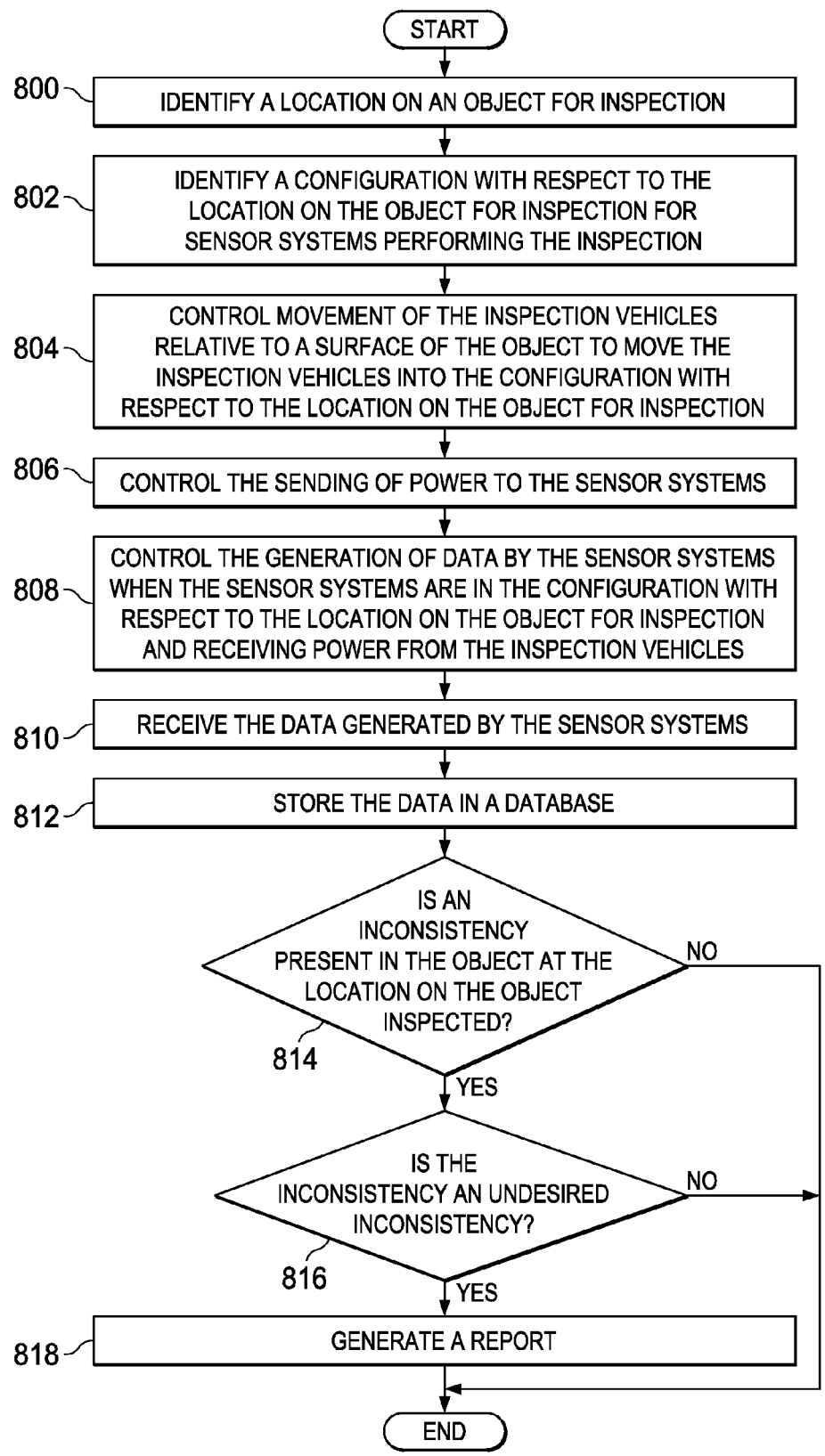
FIG. 8 is an illustration of a flowchart of a process for performing inspection of an object in accordance with an advantageous embodiment.

With reference now to FIG. 8, an illustration of a flowchart of a process for performing inspection of an object is depicted in accordance with an advantageous embodiment. The process illustrated in FIG. 8 may be implemented using inspection system 102 in FIG. 1. In particular, this process may be implemented in controller 110 in FIG. 1.

The process begins by identifying a location on an object for inspection (operation 800). Operation 800 may be performed using a model of the object. The model may be, for example, a three-dimensional computer-aided design model. In operation 800, the inspection to be performed may be non-destructive inspection.

The process identifies a configuration with respect to the location on the object for inspection for sensor systems performing the inspection (operation 802). In operation 802, locations on the object for the sensor systems are identified relative to the location on the object for inspection. In this illustrative example, the sensor systems are associated with inspection vehicles. One or more of the inspection vehicles may be implemented using inspection vehicle 200 in FIG. 2.

The process then controls movement of the inspection vehicles relative to a surface of the object to move the inspection vehicles into the configuration with respect to the location on the object for inspection (operation 804). Operation 804 may be performed by sending commands to controllers in the inspection vehicles to control the movement of the inspection vehicles.

In operation 804, the inspection vehicles are moved to the locations on the object relative to the location on the object for inspection to form the configuration identified for the sensor systems performing the inspection. The sensor systems and the inspection vehicles in the configuration identified form a mobile sensor network for performing inspections at various locations.

Next, the process controls the sending of power to the sensor systems (operation 806). In operation 806, commands are sent to the controllers in the inspection vehicles to control when power sources in the inspection vehicles send power to the sensor systems. For example, the commands may cause power to be sent to the sensor systems only when the sensor systems and the inspection vehicles are in the configuration identified.

Thereafter, the process controls the generation of data by the sensor systems when the sensor systems are in the configuration with respect to the location on the object for inspection and receiving power from the inspection vehicles (operation 808). The data is generated by a first portion of the sensor systems sending a number of signals into the object. A second portion of the sensor systems detects a number of response signals generated in response to the number of signals being sent into the object.

The locations of the first portion and the second portion of the sensor systems on the object relative to the location on the object for inspection is selected such that the number of signals generated by the first portion travel through the object at the location identified for inspection. The number of response signals may be generated in response to the number of signals traveling through the object at the location for inspection. For example, when an inconsistency is present at the location for inspection, the number of response signals may be altered from the number of signals.

The process receives the data generated by the sensor systems (operation 810). The data may be transmitted to the controller by the inspection vehicles in these illustrative examples. The process then stores the data in a database (operation 812). In operation 812, coordinates for the location of the inspection also may be stored.

Thereafter, the process determines whether an inconsistency is present in the object at the location on the object inspected (operation 814). If an inconsistency is not present, the process terminates. Otherwise, the process determines whether the inconsistency is an undesired inconsistency (operation 816). Operation 816 may be performed by applying a policy comprising a number of criteria and/or rules for when an inconsistency is an undesired inconsistency.

If the inconsistency is an undesired inconsistency, the process generates a report (operation 818), with the process terminating thereafter. Otherwise, the process just terminates. In operation 818, the report may identify at least one of the undesired inconsistency, any maintenance that needs to be performed to remove and/or rework the undesired inconsistency in the object, and other suitable information about the inspection performed. This report may be sent to a recipient, stored in a computer system, and/or some other action may be taken using the report.

The flowchart and block diagrams in the different depicted embodiments illustrate the architecture, functionality, and operation of some possible implementations of apparatuses and methods in an advantageous embodiment. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowchart or block diagrams.

In some alternative implementations of an advantageous embodiment, the function or functions noted in the block may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Turning now to FIG. 9, an illustration of a data processing system is depicted in accordance with an advantageous embodiment. In this illustrative example, data processing system 900 may be used to implement controller 110 in FIG. 1 and/or controller 212 in FIG. 2. As depicted, data processing system 900 includes communications framework 902, which provides communications between processor unit 904, memory 906, persistent storage 908, communications unit 910, input/output (I/O) unit 912, and display 914.

Processor unit 904 serves to execute instructions for software that may be loaded into memory 906. Processor unit 904 may be a number of processors, a multi-processor core, or some other type of processor, depending on the particular implementation. A number, as used herein with reference to an item, means one or more items. Further, processor unit 904 may be implemented using a number of heterogeneous processor systems in which a main processor is present with secondary processors on a single chip. As another illustrative example, processor unit 904 may be a symmetric multi-processor system containing multiple processors of the same type.

Memory 906 and persistent storage 908 are examples of storage devices 916. A storage device is any piece of hardware that is capable of storing information, such as, for example, without limitation, data, program code in functional form, and/or other suitable information either on a temporary basis and/or a permanent basis. Storage devices 916 may also be referred to as computer readable storage devices in these examples. Memory 906, in these examples, may be, for example, a random access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these examples, provides for communications with other data processing systems or devices. In these examples, communications unit 910 is a network interface card. Communications unit 910 may provide communications through the use of either or both physical and wireless communications links.

Input/output unit 912 allows for input and output of data with other devices that may be connected to data processing system 900. For example, input/output unit 912 may provide a connection for user input through a keyboard, a mouse, and/or some other suitable input device. Further, input/output unit 912 may send output to a printer. Display 914 provides a mechanism to display information to a user.

Instructions for the operating system, applications, and/or programs may be located in storage devices 916, which are in communication with processor unit 904 through communications framework 902. In these illustrative examples, the instructions are in a functional form on persistent storage 908. These instructions may be loaded into memory 906 for execution by processor unit 904. The processes of the different embodiments may be performed by processor unit 904 using computer-implemented instructions, which may be located in a memory, such as memory 906.

These instructions are referred to as program code, computer usable program code, or computer readable program code that may be read and executed by a processor in processor unit 904. The program code in the different embodiments may be embodied on different physical or computer readable storage media, such as memory 906 or persistent storage 908.

Program code 918 is located in a functional form on computer readable media 920 that is selectively removable and may be loaded onto or transferred to data processing system 900 for execution by processor unit 904. Program code 918 and computer readable media 920 form computer program product 922 in these examples. In one example, computer readable media 920 may be computer readable storage media 924 or computer readable signal media 926. Computer readable storage media 924 may include, for example, an optical or magnetic disk that is inserted or placed into a drive or other device that is part of persistent storage 908 for transfer onto a storage device, such as a hard drive, that is part of persistent storage 908.

Computer readable storage media 924 also may take the form of a persistent storage, such as a hard drive, a thumb drive, or a flash memory, that is connected to data processing system 900. In some instances, computer readable storage media 924 may not be removable from data processing system 900. In these examples, computer readable storage media 924 is a physical or tangible storage device used to store program code 918 rather than a medium that propagates or transmits program code 918. Computer readable storage media 924 is also referred to as a computer readable tangible storage device or a computer readable physical storage device. In other words, computer readable storage media 924 is a media that can be touched by a person.

Alternatively, program code 918 may be transferred to data processing system 900 using computer readable signal media 926. Computer readable signal media 926 may be, for example, a propagated data signal containing program code 918. For example, computer readable signal media 926 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some advantageous embodiments, program code 918 may be downloaded over a network to persistent storage 908 from another device or data processing system through computer readable signal media 926 for use within data processing system 900. For instance, program code stored in a computer readable storage medium in a server data processing system may be downloaded over a network from the server to data processing system 900. The data processing system providing program code 918 may be a server computer, a client computer, or some other device capable of storing and transmitting program code 918.

The different components illustrated for data processing system 900 are not meant to provide architectural limitations to the manner in which different embodiments may be implemented. The different advantageous embodiments may be implemented in a data processing system including components in addition to or in place of those illustrated for data processing system 900. Other components shown in FIG. 9 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 904 may take the form of a hardware unit that has circuits that are manufactured or configured for a particular use. This type of hardware may perform operations without needing program code to be loaded into a memory from a storage device to be configured to perform the operations.

For example, when processor unit 904 takes the form of a hardware unit, processor unit 904 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 918 may be omitted, because the processes for the different embodiments are implemented in a hardware unit.

In still another illustrative example, processor unit 904 may be implemented using a combination of processors found in computers and hardware units. Processor unit 904 may have a number of hardware units and a number of processors that are configured to run program code 918. With this depicted example, some of the processes may be implemented in the number of hardware units, while other processes may be implemented in the number of processors.

In another example, a bus system may be used to implement communications framework 902 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of devices that transmit data, receive data, or transmit and receive data. A communications unit may be, for example, a modem or a network adapter, two network adapters, or some combination thereof. Further, a memory may be, for example, memory 906, or a cache, such as found in an interface and memory controller hub that may be present in communications framework 902.

With further reference to the figures, advantageous embodiments of the disclosure may be described in the context of aircraft manufacturing and service method 1000 as shown in FIG. 10 and aircraft 1100 as shown in FIG. 11.

Turning first to FIG. 10, an illustration of an aircraft manufacturing and service method is depicted in accordance with an advantageous embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in which an advantageous embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different advantageous embodiments may be applied to other industries, such as the automotive industry.

Apparatuses and methods embodied herein may be employed during at least one of the stages of aircraft manufacturing and service method 1000 in FIG. 10.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012 and/or during maintenance and service 1014 in FIG. 10. The use of a number of the different advantageous embodiments may substantially expedite the assembly of and/or reduce the cost of aircraft 1100.

Thus, the different advantageous embodiments provide a method and apparatus for inspecting an object using a non-destructive inspection system. In one advantageous embodiment, an apparatus comprises inspection vehicles, sensor systems, and a controller. The inspection vehicles are configured to move relative to a surface of an object and transmit data generated about the object. The sensor systems are configured to generate the data about the object when the sensor systems are in a configuration with respect to a location on the object for inspection and receiving power from the inspection vehicles. The controller is configured to control movement of the inspection vehicles, control operation of the sensor systems to generate the data, and receive the data transmitted by the inspection vehicles.

In this manner, the different advantageous embodiments provide a method and apparatus for performing non-destructive inspection of an aircraft that reduces a weight and/or cost for the aircraft. For example, sensor systems associated with inspection vehicles may be used to perform inspection to reduce the weight and cost of the aircraft. Further, these sensor systems may be moved relative to the aircraft without requiring disassembly of the sensor systems and/or components in the inspection vehicles. These sensor systems also may be used with multiple aircraft.

In the illustrative examples, the sensor systems associated with the aircraft may also reduce the weight and cost of aircraft. The reduction in weight occurs by avoiding the need of additional wiring on the aircraft to provide power and communications to the sensor systems. Instead, inspection vehicles provide power and communications for these sensor systems. The communications may include sending information. The information may be, for example, commands to control the sensor systems and data received from the sensor systems.

Further, these inspection vehicles transmit the data to a controller for use in determining whether inconsistencies are present in the aircraft. The description of the different advantageous embodiments has been presented for purposes of illustration and description and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    inspection vehicles, including at least a first inspection vehicle and a second inspection vehicle, the inspection vehicles configured to be placed on a surface of an object to move relative to the surface of the object and transmit data generated about the object;
    wherein the inspection vehicles move with respect to one or more sensor systems, including a first sensor system attached to the object at a first location and a second sensor system attached to the object at a second location, the first inspection vehicle configured to provide power to the first sensor system and the second inspection vehicle configured to provide power to the second sensor system, the sensor systems configured to generate the data about the object when the sensor systems are in a configuration with respect to a location on the object for inspection and when receiving power from the inspection vehicles, the first sensor system configured to generate a signal that passes through the object and the second sensor system configured to receive the signal;
    a controller configured to control movement of the inspection vehicles, control operation of the sensor systems to generate the data, and receive the data transmitted by the inspection vehicles, the inspection vehicle configured to receive data generated about the object, and the inspection vehicle further configured to transmit received data generated about the object to the controller, and the controller configured to determine whether an undesirable inconsistency is present for the object using data generated about the object and historical data, the controller also configured to control when the first inspection vehicle provides power to the first sensor system and the second inspection vehicle provides power to the second sensor system; and
    a robotic system configured to pick up, hold, and release the inspection vehicles via one or more robotic arms.

2. The apparatus of claim 1, wherein the sensor systems are ultrasonic sensor systems in which a first portion of the ultrasonic sensor systems is configured to transmit a number of signals into the object and a second portion of the ultrasonic sensor systems is configured to receive a number of response signals generated in response to the number of signals transmitted into the object, the sensor systems configured to generate data for a surface of the object and for a structure under the surface of the object, and wherein at least one of the first inspection vehicle and the second inspection vehicle provide power to the sensor systems via wireless transmission.

3. The apparatus of claim 1, wherein the sensor systems and the inspection vehicles form a mobile sensor network when the sensor systems and the inspection vehicles are in the configuration with respect to the location on the object for the inspection, the first inspection vehicle and the second inspection vehicle each contacting a surface of the object and moving over the surface of the object.

4. The apparatus of claim 1, wherein the controller is configured to control the movement of the inspection vehicles using a model of the object.

5. The apparatus of claim 1, wherein the controller is configured to store the data in a database in association with coordinates identifying the location for which the data was generated by the sensor systems.

6. The apparatus of claim 5, wherein the database includes historical data for a number of inspections for the location performed a number of times prior to generation of the data.

7. The apparatus of claim 1, wherein the inspection vehicles transmit the data over a number of wireless communications links to the controller.

8. The apparatus of claim 1, wherein the sensor systems are configured to transmit the data to the inspection vehicles.

9. The apparatus of claim 1 further comprising:
    a movement system configured to move the inspection vehicles relative to the object, the movement system comprising a number of suction cups; and
    a positioning system configured to identify a location of the inspection vehicles relative to the object.

10. The apparatus of claim 1, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, and a building.

11. The apparatus of claim 1, wherein the controller is configured to store data generated about the object in association with coordinates for the object, and wherein the sensor systems are configured to generate data for a surface of the object and for a structure under the surface of the object.

12. The apparatus of claim 1, wherein the sensor systems are embedded within the object.

13. A health monitoring system comprising:
   a movement system associated with a hangar;
   inspection vehicles, including at least a first inspection vehicle and a second inspection vehicle, the inspection vehicles configured to be placed on a surface of an object to move relative to the surface of the object and transmit data generated about the object, wherein the first inspection vehicle and the second inspection vehicle are connected to the movement system such that the movement system places the first inspection vehicle and the second inspection vehicle onto a surface of an aircraft;
   wherein the inspection vehicles move with respect to one or more sensor systems, including a first sensor system associated with the first inspection vehicle and a second sensor system associated with the second inspection vehicle, the sensor systems associated with the inspection vehicles, wherein the sensor systems are configured to generate the data about the object, the first sensor system configured to generate a signal that passes through the object and the second sensor system configured to receive the signal; and
   a controller configured to control movement of the inspection vehicles into a configuration with respect to a location for inspection, control operation of the sensor systems to generate the data about the object for the location, and receive the data transmitted by the inspection vehicles, the sensor system configured to transmit data generated about the object to the inspection vehicles, and the inspection vehicles configured to transmit received data generated about the object to the controller, the controller storing data generated about the object in association with coordinates for the object, the controller configured to determine whether an undesirable inconsistency is present for the object using data generated about the object and historical data about the object pursuant to a policy;
   wherein the inspection vehicles transmit the data over a number of wireless communications links to the controller; and
   a robotic system configured to pick up, hold, and release the inspection vehicles via one or more robotic arms.

14. A method for inspecting an object, the method comprising:
   controlling, using a controller, movement of inspection vehicles placed on a surface of the object relative to the surface of the object, the object having a first sensor system and a second sensor system, the inspection vehicles including at least a first inspection vehicle and a second inspection vehicle, the controller configured to move the first inspection vehicle so as to associate with the first sensor system and to move the second inspection vehicle so as to associate with the second sensor system, wherein the inspection vehicles are moved with respect to the sensor systems;
   controlling when the first inspection vehicle provides power to the first sensor system and when the second inspection vehicle provides power to the second sensor system;
   controlling, using the controller, generation of data about the object by sensor systems, including a first sensor system associated with the first inspection vehicle and a second sensor system associated with the second inspection vehicle, the sensor systems configured to generate the data when the sensor systems are in a configuration with respect to a location on the object for inspection and receiving power from the inspection vehicles, the first sensor system configured to generate a signal that passes through the object and the second sensor system configured to receive the signal;
   transmitting, by the sensor system, data generated about the object to the inspection vehicles;
   transmitting, by the inspection vehicles, data generated about the object to the controller;
   storing the data generated by the sensor systems;
   determining whether an undesired inconsistency is present at the location on the object using the data generated about the object; and
   picking up, holding, and releasing the inspection vehicles via one or more robotic arms of a robotic system;
   wherein the inspection vehicles transmit the data over a number of wireless communications links to the controller.

15. The method of claim 14, wherein the step of determining whether the undesired inconsistency is present at the location on the object using the data comprises:
   determining whether an inconsistency identified using the data and historical data generated for the object at times prior to the generation of the data is the undesired inconsistency, the determining including using a policy.

16. The method of claim 14, wherein the step of controlling the generation of the data about the object by the sensor systems configured to generate the data when the sensor systems are in the configuration with respect to the location on the object for the inspection and receiving the power from the inspection vehicles comprises:
   causing a first portion of the sensor systems to transmit a number of signals into the object; and
   causing a second portion of the sensor systems to detect a number of response signals generated in response to the number of signals transmitted into the object, wherein the number of response signals forms the data.

17. The method of claim 14, wherein the sensor systems are associated with the object at locations on the object and wherein the step of controlling, using the controller, the movement of the inspection vehicles relative to the surface of the object comprises:
   controlling the inspection vehicles to move to the locations on the object, the locations associated with coordinates for the object, wherein the inspection vehicles are configured to send the power to the sensor systems when the inspection vehicles are at the locations on the object.

18. The method of claim 14, wherein the sensor systems are associated with the inspection vehicles and wherein the step of controlling, using the controller, the movement of the inspection vehicles relative to the surface of the object comprises:
   identifying the location for the inspection using a model of the object; and
   controlling the inspection vehicles to move into the configuration with respect to the location for the inspection.

19. The method of claim 14, wherein the step of storing the data generated by the sensor systems comprises:
   storing the data in a database in association with coordinates identifying the location for which the data was generated by the sensor systems.

20. An inspection system to inspect an aircraft in a hangar, the inspection system comprising:
   a movement system associated with the hangar, the movement system comprising a robotic system;
   the robotic system configured to pick up, hold, and release one or more inspection vehicles via one or more robotic arms;
   the robotic arms configured to place the inspection vehicles onto a surface of the aircraft;
   the inspection vehicles, once placed onto the aircraft, configured to move on the surface to different locations on the aircraft to perform non-destructive inspection;
   one or more sensor systems embedded within the aircraft, the sensor systems configured to receive power from the inspection vehicles when power sources of the inspection vehicles come into contact with the sensor systems;
   a controller configured to receive, from the inspection vehicles, data generated during the non-destructive inspection using wireless communication and configured to send locations for inspection to the robotic system; and
   a track and crane system wherein a crane of the track and crane system is configured to hold and move the robotic system and the crane is configured to move along a track of the track and crane system with respect to the aircraft.

* * * * *